United States Patent
Undén et al.

(10) Patent No.: US 10,954,461 B2
(45) Date of Patent: Mar. 23, 2021

(54) METHODS FOR PREVENTING MICROBIAL GROWTH AND MICROBIOLOGICALLY INFLUENCED CORROSION IN A BIODEGRADABLE AND/OR RENEWABLE FUEL, HYDRAULIC FLUID AND/OR LUBRICANT

(71) Applicant: TRIBORON INTERNATIONAL AB, Kista (SE)

(72) Inventors: Magnus Undén, Lidingö (SE); Ian Field, Abingdon (GB); Kristina Olsson, Lidingö (SE)

(73) Assignee: Triboron International AB, Kista (SE)

( * ) Notice: Subject to any disclaimer, the term of this patent is extended or adjusted under 35 U.S.C. 154(b) by 36 days.

(21) Appl. No.: 16/345,144

(22) PCT Filed: Oct. 27, 2017

(86) PCT No.: PCT/SE2017/051055
§ 371 (c)(1),
(2) Date: Apr. 25, 2019

(87) PCT Pub. No.: WO2018/080388
PCT Pub. Date: May 3, 2018

(65) Prior Publication Data
US 2019/0284492 A1 Sep. 19, 2019

(30) Foreign Application Priority Data
Oct. 27, 2016 (SE) .................................... 1651410-1

(51) Int. Cl.
*C10L 10/04* (2006.01)
*A01N 59/14* (2006.01)
(Continued)

(52) U.S. Cl.
CPC .............. *C10L 10/04* (2013.01); *A01N 59/14* (2013.01); *A61L 2/18* (2013.01); *C10L 1/10* (2013.01);
(Continued)

(58) Field of Classification Search
CPC .... C10L 10/04; C10L 1/10; C10L 2200/0484; C10L 2250/02; C10L 1/1291;
(Continued)

(56) References Cited

U.S. PATENT DOCUMENTS

| 8,546,386 B2 | 10/2013 | Green et al. |
| 2007/0232504 A1 | 10/2007 | Goyal et al. |
| 2012/0108475 A1* | 5/2012 | Lindblom ............ C10M 125/26 508/156 |

FOREIGN PATENT DOCUMENTS

WO    2010/134872    11/2010

OTHER PUBLICATIONS

Zhang et al. "Case Study of Biodiesel-Diesel Blends as a Fuel in Marine Environment", Advances in Chemical Engineering and Science 1:65-71 (2011).
(Continued)

*Primary Examiner* — Taiwo Oladapo
(74) *Attorney, Agent, or Firm* — Myers Bigel, P.A.

(57) ABSTRACT

Fuels, hydraulic fluids and lubricants made of or comprising a portion of renewable hydrocarbon raw materials, as well as biodegradable fuels, hydraulic fluids and lubricants are known to support microbial growth. Highly toxicorganic biocides have been added to reduce microbial growth. The use of such biocides can now be avoided, by instead using a stable solution of boric acid in a solvent, the boric acid being completely dissolved or at least free from any particles larger than 100 nm in size, and adding this solution to the fuel, hydraulic fluid or lubricant to give a final concentration
(Continued)

of boron in the range of 1-100 ppm, preferably 1-50 ppm in the product. While preventing microbial growth, the addition of boron also reduces corrosion, in particular microbiologically induced corrosion (MIC).

2 Claims, 2 Drawing Sheets

(51) Int. Cl.
| | |
|---|---|
| *A61L 2/18* | (2006.01) |
| *C10L 1/12* | (2006.01) |
| *C10M 109/02* | (2006.01) |
| *C10M 125/26* | (2006.01) |
| *C10M 169/04* | (2006.01) |
| *C10L 1/10* | (2006.01) |
| *C10L 1/182* | (2006.01) |
| *C10N 20/06* | (2006.01) |
| *C10N 20/00* | (2006.01) |
| *C10N 30/12* | (2006.01) |
| *C10N 30/16* | (2006.01) |
| *C10N 30/00* | (2006.01) |
| *C10N 40/08* | (2006.01) |

(52) U.S. Cl.
CPC .......... *C10L 1/1291* (2013.01); *C10M 109/02* (2013.01); *C10M 125/26* (2013.01); *C10M 169/04* (2013.01); *C10L 1/1824* (2013.01); *C10L 2200/0423* (2013.01); *C10L 2200/0446* (2013.01); *C10L 2200/0469* (2013.01); *C10L 2200/0476* (2013.01); *C10L 2230/083* (2013.01); *C10L 2250/06* (2013.01); *C10M 2201/086* (2013.01); *C10M 2201/087* (2013.01); *C10M 2207/2805* (2013.01); *C10M 2207/401* (2013.01); *C10M 2209/1033* (2013.01); *C10N 2020/06* (2013.01); *C10N 2020/081* (2020.05); *C10N 2030/12* (2013.01); *C10N 2030/16* (2013.01); *C10N 2030/44* (2020.05); *C10N 2040/08* (2013.01)

(58) Field of Classification Search
CPC ....... C10L 2200/0476; C10L 2230/083; C10L 2250/06; C10L 1/1824; C10L 2200/0423; C10L 2200/0446; C10L 2200/0469; A01N 59/14; A61L 2/18; C10M 109/02; C10M 125/26; C10M 169/04; C10M 2209/1033; C10M 2207/2805; C10M 2201/086; C10M 2201/087; C10M 2207/401; C10N 2030/64; C10N 2020/06; C10N 2020/081; C10N 2030/12; C10N 2030/16; C10N 2030/44; C10N 2040/08
See application file for complete search history.

(56) References Cited

OTHER PUBLICATIONS

Biobor Jf, Microbiocide, Technical Data Sheet—TD-9610, 2011, [online], [retrieved on Apr. 28, 2017] Retrieved from the Internet: URL: http://www.biobor.com/Biobor-Resources/Brochures/BioborJF%20Technical%20Data.pdf.

Repetto et al. "Current and Potential Aviation Additives for Higher Biofuel Blends in Jet A-1", Biofuels for Aviation, 1st Ed. Chp. 12:261-275 (2016).

Borokhov et al. "Antimicrobial Properties of Boron Derivatives", ACS Symposium Series, 2007, Sep., vol. 967, New Biocides Development, Chapter 20, pp. 412-435.

International Search Report and Written Opinion corresponding to International Application No. PCT/SE2017/051055 dated Jan. 22, 2018.

* cited by examiner

METHODS FOR PREVENTING MICROBIAL GROWTH AND MICROBIOLOGICALLY INFLUENCED CORROSION IN A BIODEGRADABLE AND/OR RENEWABLE FUEL, HYDRAULIC FLUID AND/OR LUBRICANT

STATEMENT OF PRIORITY

This application is a 35 U.S.C. § 371 national phase application of PCT Application No. PCT/SE2017/051055 filed Oct. 27, 2017, which claims priority to Swedish Application No, 1651410-1 filed Oct. 27, 2016. the entire contents of each of which is incorporated by reference herein.

TECHNICAL FIELD

The present disclosure relates generally to methods and compositions for preventing microbial growth in a fuel, hydraulic fluid and/or lubricant, and in particular for the prevention of microbial growth in a biodegradable and/or renewable fuel, hydraulic fluid and/or lubricant. The disclosure also relates to the prevention of corrosion, such as microbiologically influenced corrosion (MIC) on surfaces and in equipment in contact with a fuel, hydraulic fluid and/or lubricant, in particular a biodegradable and/or renewable fuel, hydraulic fluid and/or lubricant.

BACKGROUND

Starting from the onset of the industrial revolution, fossil fuels have supplied energy for production, transport and heating and satisfied a growing global demand for energy. A transition from coal to oil and further to natural gas as well as the introduction of new efficient technology has helped to reduce the environmental impact of using fossil fuels. It however remains a fact that fossil fuels release carbon dioxide, nitrogen dioxide, sulphur dioxide, carbon monoxide and other pollutants when burnt, and that these have severe consequences on the environment, including the global climate. Further, fossil fuels are non-renewable sources of energy, currently being depleted at a fast rate. Switching to renewable sources for the production of fuels has become a necessity.

Consequently there has been a significant increase in the use of renewable and less environmentally harmful fuels during the last decades of the $20^{th}$ century. Bioethanol and vegetable oils are currently among the main alternatives, but also synthetic methanol, biogas and hydrogen are increasingly used. An important benefit of vegetable oils and bioethanol is however that they can be mixed into conventional diesel and petrol, respectively, thus reducing the consumption of fossil fuels without the need of any far-reaching conversion of engines or the fuel distribution systems.

The past decades have also witnessed the introduction of biodegradable and/or renewable hydraulic fluids and lubricants, for example fluids and greases for mobile or marine hydraulic and propulsion systems operating in environmentally sensitive areas. Examples include, but are not limited to equipment for use in agriculture and forestry, recreational and commercial boating, in vessels and equipment used in shipping, fishing and fish farming, off-shore construction and oil and gas exploration, wave and tidal power, and off-shore wind power.

The present disclosure relates to all fuels, hydraulic fluids and lubricants prone to support microbial growth, but primarily focuses on fuels, hydraulic fluids and lubricants which are either biodegradable, made from renewable raw materials, or contain such biodegradable and/or renewable components.

Biofuels

Ethanol is currently one of the most preferred biofuels, in part because it is significantly less polluting than gasoline. Importantly, the combustion of ethanol does not produce any sulphur dioxide or lead emissions. Further, the carbon dioxide produced is at least partially offset by growing fermentable crops, such as sugar canes, corn, cassava, potato etc. Importantly, ethanol can be mixed into gasoline, and the normal distribution system can thus be used. In the European Union, the common gasoline specification EN-228 allows an addition up to 10% v/v ethanol. A usual ratio is 5% ethanol to 95% gasoline, known as E5, but most cars could run on about 10% ethanol in gasoline.

In countries such as Brazil, a higher ethanol content is mandatory, and since 2007 the legal blend is 25% ethanol and 75% gasoline, known as E25. There are also vehicles that run on neat ethanol fuel, E100. In Europe, E85 is an important fuel blend and used in vehicles specially adapted for this fuel. Ethanol-gasoline blends are sometimes referred to as "flex fuel" as the ethanol content may vary, in particular in colder climates. According to the American standard ASTM 5798, the ethanol content may vary between 51 to 83%.

Ethanol is also increasingly being added to diesel fuel. One example is the commercial blend known as ED95. This is an ethanol based fuel for adapted diesel engines. It consists of 95 percent ethanol with the addition of ignition improvers, denaturants, lubricants and anticorrosive additives. According to manufacturer's specifications and analysis certificates (SEKAB), ED95 contains a minimum of 92.4% per weight ethanol, 5.0% per weight ignition improvers, 2.15% per weight methyl tert-butyl ether (MTBE), about 0.5% per weight isobutanol, about 1% per weights lubricant, and 90 ppm corrosion inhibitor, and coloring agent. One example of lubricant is 2,2'-(octadec-9-en-1-ylimino)diethanol.

Methanol is another alternative non-fossil fuel that can be used in internal combustion engines, either in combination with gasoline, or as such. Methanol can be produced from biomass, but also synthesized from carbon dioxide and hydrogen. Methanol is already widely used in race cars, and its use for private and commercial vehicles is slowly increasing in both China and the USA. At high levels, methanol is corrosive to certain materials commonly used in engines and fuel lines, but in low concentrations there are no adverse effects. A high-level blend such as M85 (85% methanol and 15% gasoline) however requires modifications to be made to the engine. Methanol is also being investigated for marine applications. Methanol can also be converted into dimethyl ether (DME) and used as a diesel replacement.

In addition to ethanol and methanol, biodiesel is growing in importance as a fuel. The term biodiesel refers to a fuel comprised of mono-alkyl esters of long chain fatty acids derived from vegetable oils or animal fats. One group is referred to as fatty acid methyl esters (FAME) which have physical properties similar to those of conventional diesel fuel. Rapeseed methyl ester (RME) is a commonly used FAME in Europe. A common European standard for biodiesel, including FAME, is EN 14214, another is EN 16709.

HEFA (Hydroprocessed Esters and Fatty Acids), also called HVO (Hydrotreated Vegetable Oil), is a renewable diesel fuel that can be produced from a wide array of vegetable oils and fats. The term HEFA or HVO is currently used collectively for these biogenic hydrocarbon-based renewable biofuels. The composition of HVO is regulated in standard EN 15940, and it is free of aromatics, sulfur and has a high cetane number. It is a so-called drop-in fuel, meaning that it is chemically equivalent to fossil diesel fuel and can be used in existing diesel engines without technical blend walls.

In order to be called biodiesel, a fuel must meet the requirements of national and international standards, for example EN-590 and ASTM D 6751, which gives specifications for biodiesels blended with middle distillate fuels, including various test methods to be used in the determination of certain properties for biodiesel blends. The term "biodiesel blend" refers to a blend of biodiesel fuel meeting EN-590 or ASTM D 6751 and a petroleum-based diesel fuel. This is often designated BXX, where XX represents the volume percentage of biodiesel fuel in the blend. The maximum allowed biodiesel content in EN590 is 7% v/v.

It was initially believed that biofuels would have a non-corrosive nature due to the low electrical conductivity, but unfortunately practical experience has proven this hypothesis to be wrong. Different types of corrosion issues have been encountered for biofuels with different origin, e.g. stress-corrosion cracking (SCC) for the combination carbon steel with fuel grade ethanol (FGE) has been observed in USA but not in Brazil. Furthermore, corrosion correlated to bioethanol is more extensive than with biodiesel.

Importantly, microbiologically influenced corrosion (MIC) is the main corrosion type observed for the biodiesel system, especially in the presence of moist air or accumulation of water. The biological origin of biodiesel together with the presence of water are the primary reasons for the higher potential for supporting microbial activities, compared to fossil-based diesel.

Biogas is also increasingly finding uses as a fuel for cars, trucks, busses, and heavy equipment such as construction equipment, generators and ships. To the extent applicable, this disclosure also refers to the prevention of microbial growth in systems for the production, handling, storage, transport, distribution, dispensing and use of biogas.

Hydraulic Fluids

Hydraulic fluids or hydraulic liquids are the medium by which power is transferred in hydraulic machinery. The main requirement is that a hydraulic fluid has low compressibility, preferably as close to zero as possible, but it is also important that the fluid helps to lubricate the equipment and also prevents corrosion. Recently, the environmental impact has become a focus of attention, and low toxicity and biodegradability are important features for example in the case of leakage and spills.

According to an article by T, Marougy (Hydraulic fluids can help you go 'green', in Hydraulics & Pneumatics, Oct. 9, 2012) there are four basic types of environmentally-friendly hydraulic fluids in common use:

HETG: hydraulic environmental triglyceride (water insoluble triglycerides),
HEES: hydraulic environmental ester synthetic (water insoluble synthetic ester),
HEPG: hydraulic environmental poly glycol (water soluble poly alkylene glycol [PAG]), and
HEPR: hydraulic environmental polyalphaolefin and related fluids (water insoluble poly alpha olefins [PAO] and related hydrocarbon-based fluids).

HETG fluids (hydraulic environmental triglyceride) are water insoluble triglycerides derived from vegetable or animal oils—with soybean, sunflower, and rapeseed (Canola) being the most common sources. They frequently contain soluble thickeners to increase their natural viscosity, which is approximately 35 mm$^2$/sec at 40° C. Triglycerides are long-chain fatty acids combined with alcohol in the form of glycerin. Natural triglycerides have excellent lubricity but poor thermal and hydrolytic stability. They also oxidize rapidly. Additives, chemical modification, and even genetic modification of the seeds used to produce the base stock can improve hydrolytic stability and oxidation resistance.

HETG fluids offer many advantages. For one, they are highly biodegradable and nontoxic. They offer excellent lubricity and anticorrosion properties. And because they are made from natural, renewable resources, they are readily available. In addition, they have a high viscosity index and high flash point. But HETG fluids also have drawbacks. High-temperature operation can cause quick aging, rapid oxidation, and extreme thickening and gumming. In addition, they are susceptible to water contamination, which causes hydrolysis and increases total acid number (TAN). They tend to thicken and gel at low temperature, which hurts machine performance. And because they are miscible with mineral oil, this can lower biodegradability in circuits that aren't properly flushed. Finally, they are currently significantly more expensive than mineral oils.

HEES fluids (hydraulic environmental ester synthetic) are water-insoluble synthetic esters derived from either petroleum or vegetable (typically rapeseed) oil feedstocks. Petroleum-sourced HEES fluids combine an organic acid and alcohol, whereas vegetable sourced fluids combine a fatty acid and alcohol. HEES fluids are available as unsaturated, partially saturated, and fully saturated products. Of these, fully saturated versions generally offer the best performance and command the highest price.

HEES fluids offer long service life due to high thermal and oxidative stability and good fluidity at low temperatures. They are also available in a broad viscosity range (ISO VG 32/46/68). However, they have more disadvantages than advantages. For example, they're expensive and, like HETG fluids, require special system-design requirements. They also hydrolyze in the presence of water. And like HETG, because they are miscible with mineral oil, they can become contaminated with mineral oils, resulting in decreased biodegradability.

HEPG fluids (hydraulic environmental poly glycol) are water-soluble polyalkylene glycols (PAG), polymers made from reacting alkylene-oxide monomers such as ethylene oxide, propylene glycol, or propylene oxide with glycol. Those with 50 to 100% ethylene oxide are water soluble, while those with 100% propylene oxide are water insoluble. Both types are inherently fire resistant.

The biodegradability of HEPG fluids depends on the ratio of propylene to ethylene oxides. The higher the molecular weight, the lower the biodegradability of the fluid. HEPG fluids come in a broad viscosity range and have an operating temperature range of −20 to 80° C. In addition, water-soluble polyglycols can be used as anhydrous lubricants. However, they require special system designs. For instance, they are incompatible with polyurethane seals, and pumps and motors may need to be derated when used with HEPG fluids.

HEPR fluids (hydraulic environmental polyalphaolefin and related) are water-insoluble polyalphaolefins (PAO) and related hydrocarbon-based fluids. These synthetic hydrocarbons are made by polymerizing alpha olefins to produce PAO. Only low viscosity polyalphaolefins are considered environmentally friendly.

A key advantage of HEPR fluids is that they offer excellent oxidation stability and good corrosion protection. They also have good lubricity and aging characteristics, and a long service life. They offer good viscosity performance over a wide temperature range: pour point is −20 to −40° C. and operating temperature range is −30 to 100° C. However, like most green fluids, they can be costly and are incompatible with many seal and gasket materials.

Some bio fluids, particularly HEES and HETG types, are susceptible to water contamination, which degrades fluid properties. They readily absorb water and, if water remains in the fluid, it will hydrolyze the bio fluid. The fluid will break down and lose lubricity, and its acidity will increase leading to problems with corrosion. It's therefore essential to closely monitor water content and acid levels in vegetable based and synthetic bio fluids.

Lubricants

Vegetable oils and fats have been used as lubricants since ancient times, and gained renewed interest in times of war and oil shortages during the $20^{th}$ century. In recent years, a conscious effort to increase the use of renewable hydrocarbons, as well as an ambition to minimize the environmental impact, has led to a growing focus on vegetable oils. The advantages are clear, vegetable oils are biodegradable, in general less toxic, and can be made from renewable sources. There are however disadvantages, such as insufficient oxidation stability, and a tendency for microbial growth and degradation, in particular in the interface between the lubricant and water condensate forming in tanks and pipes.

Examples of biodegradable lubricants include vegetable oils such as rapeseed oil, sunflower oil, soybean oil, etc in different mixtures, as well as synthetic esters.

The consequences of microbial growth in hydraulic fluids and lubricants can be severe, leading to clogging of filters and valves, reduced heat exchange and over heating of engines, increased acidity of the hydraulic fluid or lubricant, increased corrosion etc. Curbing the microbial infection and restoring the system or engine requires considerable work, and it may include harsh heat treatment, the addition of highly toxic biocides and frequently also a complete manual cleaning of tanks, pipes and components.

In U.S. Pat. No. 6,783,561, Ali Erdemir presents a method for providing enhanced lubricity in fuels and lubricants wherein a boron compound is added to said fuel or lubricant. Erdemir is focused on reducing or eliminating sulfur in the fuel, and has investigated the anti-wear properties of low-sulfur fuel with different additions of boron. Erdemir suggests boron concentrations from about 30 ppm to about 3000 ppm, about 200 to about 2000 ppm, alternatively from about 50 to about 1000 ppm or from about 100 ppm to about 500 ppm.

The earlier technology however did not fulfill the expectations. Problems with the stability of boron solutions, i.e. a tendency of aggregation and sedimentation, have hampered the large scale use of boron containing additives for lubrication purposes. Therefore, Tommy Lindblom and Magnus Undén developed a method for producing stable boric solutions, disclosed in international patent application WO 2010/134872 and patented for example as U.S. Pat. No. 9,222,045. This method addresses the difficulties in producing a stable boric solution, i.e. avoiding aggregation and precipitation during storage. The method results in a boron solution which is stable over time. According to their findings, the finished fuel, after adding the additive produced by their method, should reach a boron concentration within the range 10-10 000 ppm, preferably within the range 20-30 ppm. A higher concentration, up to 10 000 ppm pertains primarily to use in more solid lubricants. An antibacterial effect is only mentioned in the connection with the use of a boron solution as cutting fluid. It is clear from this context that it is the boron solution as such that is believed to have an antibacterial effect when used as a cutting fluid, and not as an additive to a lubricant. This is clear from the phrase "The solution may also serve as an oil-free lubricant for the metal pressing industry, making it possible to eliminate oil recovery after the pressing process." (Emphasis added)

An international patent application, WO 2005/083042, presents an additive for two-stroke engines where the amount of oil is reduced and a lubricating effect is achieved by an addition of boron. It is suggested that 10-90% of the oil is replaced by fuel or a hydrocarbon carrier, for example an alcohol. According to a preferred embodiment, only 10-60% of the oil is replaced, and the boron content of the additive is in the range 1500-2500 ppm. The application contains no examples.

In a case study of the use of biodiesel-blends as fuel in marine environments, the authors found that excessive sludge formation and fuel filter clogging constituted a problem, and it was suggested that bacterial contamination was one of the major factors in contribution to the sludge formation (T. X. Zhang et al., Advances in Chemical Engineering and Science, 2011, 1, 65-71). In this case study, a commercial biocide (BIOBOR JF®) was added to the fuel.

According to the Safety Data Sheet (BIOBOR JF® SDS, Hammonds Fuel Additives Inc., Preparation date: 1 Jan. 2013, Revision date: 3 Aug. 2015) the major active ingredients are 2,2'-(1-methyltrimethylenedioxy)-bis-(4-methyl-1,3,2-dioxaboriane) and 2,2'-oxybis(4,4,6-trimethyl-1,3,2-dioxaboriane) which are toxic organic boron-containing biocides.

SUMMARY

The present inventors have surprisingly found that boron and/or boric acid in extremely low concentrations not only have friction reducing properties, as previously disclosed, but also significant antimicrobial effect, as well as corrosion reducing or preventing effect. These effects are important in all fuels, hydraulic fluids and lubricants, but particularly important and valuable in biofuels and in biologically degradable hydraulic fluids and lubricants, which are more prone to microbial growth, and where the use of traditional antimicrobial compounds needs to be minimized or entirely avoided. Further, boron and/or boric acid can be used both to "kill off" microbes in fuels, hydraulic fluids and lubricants, and to maintain an environment free of microbes. This effect can also be defined as the conservation of a fuel, hydraulic fluid and/or lubricant, as the boron and/or boric acid makes it possible to store said fuel, hydraulic fluid and/or lubricant for long periods of time without reductions in quality.

Thus, as a first aspect of this disclosure, the inventors present the use of an inorganic boron compound for preventing microbial growth in fuels, hydraulic fluids and lubricants, in particular in biofuels and biologically degradable hydraulic fluids and lubricants, wherein boron is added to said fuel and/or hydraulic fluid and/or lubricant to give a final concentration of elemental boron in the interval of 1 to 100 ppm.

According to an embodiment of said first aspect, said biofuel is chosen from biogas, an ethanol/gasoline blend, ethanol, an methanol/gasoline blend, methanol, an ethanol/diesel blend, a biodiesel according to EN-590 or ASTM D 6751, a blend of biodiesel and petroleum-based diesel, or mixtures thereof.

According to a preferred embodiment, the boron is added in the form of a stable solution of boric acid in a solvent, free from any particles larger than 100 nm, and wherein said stable solution containing boron is added to give a final concentration of elemental boron in the interval of 1 to 100 ppm, preferably 1-50 ppm and most preferably 1 to 10 ppm.

Most preferably, where the biofuel is chosen from biogas, an ethanol/gasoline blend, ethanol, an methanol/gasoline blend, methanol, an ethanol/diesel blend, a biodiesel according to EN-590 or ASTM D 6751, a blend of biodiesel and petroleum-based diesel, or mixtures thereof, said boron is added to give a final concentration of elemental boron in the interval of 1 to 100 ppm, preferably 1-50 ppm and most preferably 1 to 10 ppm.

According to a particular embodiment, wherein said biofuel is biogas, the boron is added in the form of a stable solution of boric acid in a solvent, free from any particles larger than 100 nm, and wherein said boron and/or boric acid solution is applied on the inner surfaces of compressors, pumps, valves, pipes and storage tanks.

According to a particular embodiment, wherein said biologically degradable hydraulic fluid is chosen from a hydraulic environmental triglyceride (HETG), a hydraulic environmental ester synthetic (HEES, a water insoluble synthetic ester), hydraulic environmental poly glycol (HEPG), and hydraulic environmental polyalphaolefins (HEPR).

Preferably said biologically degradable hydraulic fluid is a hydraulic fluid chosen from hydraulic fluids according to SS 155434 (National Swedish standard for hydraulic fluids).

In the use according to any one of the previous embodiments, the boron and/or boric acid solution is added to the hydraulic fluid in the form of a stable solution of boric acid in a solvent free from any particles larger than 100 nm, and wherein said boron is added to give a final concentration of elemental boron in the interval of 1 to 100 ppm.

According to another embodiment, said biologically degradable lubricant is chosen from a lubricant having a base oil chosen from a vegetable oil, a synthetic ester, and polyalkylene glycols.

Preferably the lubricant comprises a vegetable base oil chosen from rapeseed oil, soybean oil, sunflower oil, palm oil, and mixtures thereof.

Preferably said biologically degradable lubricant is a lubricant chosen from lubricants according to SS 155470 (National Swedish Standard for greases).

According to an embodiment, the boron is added to the lubricant in the form of a stable solution of boric acid in a solvent, free from any particles larger than 100 nm, and wherein said boron is added to give a final concentration of elemental boron in the interval of 1 to 100 ppm.

A second aspect relates to the use of an inorganic boron compound for preventing microbial growth and microbiologically influenced corrosion (MIC) in engines and in equipment operating on, in contact with, or used for the storage and/or transportation of a biofuel and/or a biologically degradable hydraulic fluid and/or lubricant.

According to an embodiment of said second aspect, the biofuel is chosen from biogas, an ethanol/gasoline blend, ethanol, an methanol/gasoline blend, methanol, an ethanol/diesel blend, a biodiesel according to EN-590 or ASTM D 6751, a blend of biodiesel and petroleum-based diesel, or mixtures thereof.

Preferably the boron is added in the form of a stable solution of boric acid or boron oxide in a solvent, free from any particles larger than 100 nm, and wherein said stable solution is added to give a final concentration of elemental boron in the interval of 1 to 100 ppm, preferably 1-50 ppm and most preferably 1 to 10 ppm.

More preferably the boron is added to give a final concentration of elemental boron in the interval of 1-10 ppm.

According to another embodiment, the biofuel is biogas, the inorganic boron compound is added in the form of a stable solution of boric acid in a solvent, free from any particles larger than 100 nm, and wherein said boron is applied on the surfaces of compressors, pumps, valves, pipes and storage tanks.

According to another embodiment, where the biofuel is an ethanol/gasoline blend or ethanol, the inorganic boron compound is added to the biofuel in the form of a stable solution of boric acid or boron oxide in a solvent, free from any particles larger than 100 nm, and wherein said solution is added to give a final concentration of elemental boron in the interval of 1 to 100 ppm, preferably 1-50 ppm and most preferably 1 to 10 ppm.

In another embodiment, said biologically degradable hydraulic fluid is chosen from a hydraulic environmental triglyceride (HETG), a hydraulic environmental ester synthetic (HEES, a water insoluble synthetic ester), hydraulic environmental poly glycol (HEPG), and hydraulic environmental polyalphaolefins (HEPR).

In one embodiment, said biologically degradable hydraulic fluid is a hydraulic fluid chosen from hydraulic fluids according to SS 155434 (National Swedish standard for hydraulic fluids).

Preferably the boron is added to the hydraulic fluid in the form of a stable solution of boric acid in a solvent, free from any particles larger than 100 nm, and wherein said boron is added to give a final concentration of elemental boron in the interval of 1-100 ppm.

Most preferably the boron is added to give a final concentration of elemental boron in the interval of 1-10 ppm.

According to another embodiment, said biologically degradable lubricant is chosen from a lubricant having a base oil chosen from a vegetable oil, a synthetic ester, and polyalkylene glycols.

Preferably the lubricant comprises a vegetable base oil chosen from rapeseed oil, soybean oil, sunflower oil, palm oil, and mixtures thereof.

According to an embodiment, said biologically degradable lubricant is a lubricant chosen from lubricants according to SS 155470 (National Swedish Standard for greases).

In the above embodiments, the boron is added to the lubricant in the form of a stable solution of boric acid in a solvent, free from any particles larger than 100 nm, and said stable solution is added to give a final concentration of elemental boron in the interval of 1 to 100 ppm.

A third aspect relates to a method for the conservation of fuels, hydraulic fluids and lubricants, for the prevention of microbial growth in fuels, hydraulic fluids and lubricants, in particular in a biofuel, a biologically degradable hydraulic fluid or lubricant, wherein an inorganic boron compound is added to said fuel and/or hydraulic fluid and/or lubricant to give a final concentration of elemental boron in the interval of 1 to 100 ppm. Embodiments of said third aspect are defined as set out for the embodiments of the first aspect, presented above. Said embodiments are also defined in the claims, incorporated herein by reference.

A fourth aspect relates to a method for the prevention of microbial growth and microbiologically induced corrosion (MIC) in equipment operating on or used for the storage and/or transport of a fuel, a hydraulic fluid or lubricant, and in particular a biofuel, biologically degradable hydraulic fluid or lubricant. Embodiments of said fourth aspect are defined as set out for the embodiments of the first aspect, presented above. Said embodiments are also defined in the claims, incorporated herein by reference.

A fifth aspect relates to a gasoline-based fuel blend comprising at least 5% ethanol and 1-10 ppm elemental boron, preferably in the form of an inorganic boron compound.

A sixth aspect relates to a gasoline-based fuel blend comprising at least 5% methanol and 1-10 ppm elemental boron, preferably in the form of an inorganic boron compound.

A seventh aspect relates to a biodiesel fuel blend comprising 1-10 ppm elemental boron, preferably in the form of an inorganic boron compound.

An eight aspect relates to a biodegradable hydraulic fluid comprising 1-100 ppm elemental boron, preferably in the form of an inorganic boron compound.

A ninth aspect relates to a biodegradable lubricant comprising a vegetable base oil and 1-100 ppm elemental boron, preferably in the form of an inorganic boron compound.

Further aspects and embodiments thereof will become apparent to a skilled person upon study of the description, drawings, examples and the claims, incorporated herein.

DESCRIPTION OF EMBODIMENTS

Figure 1:
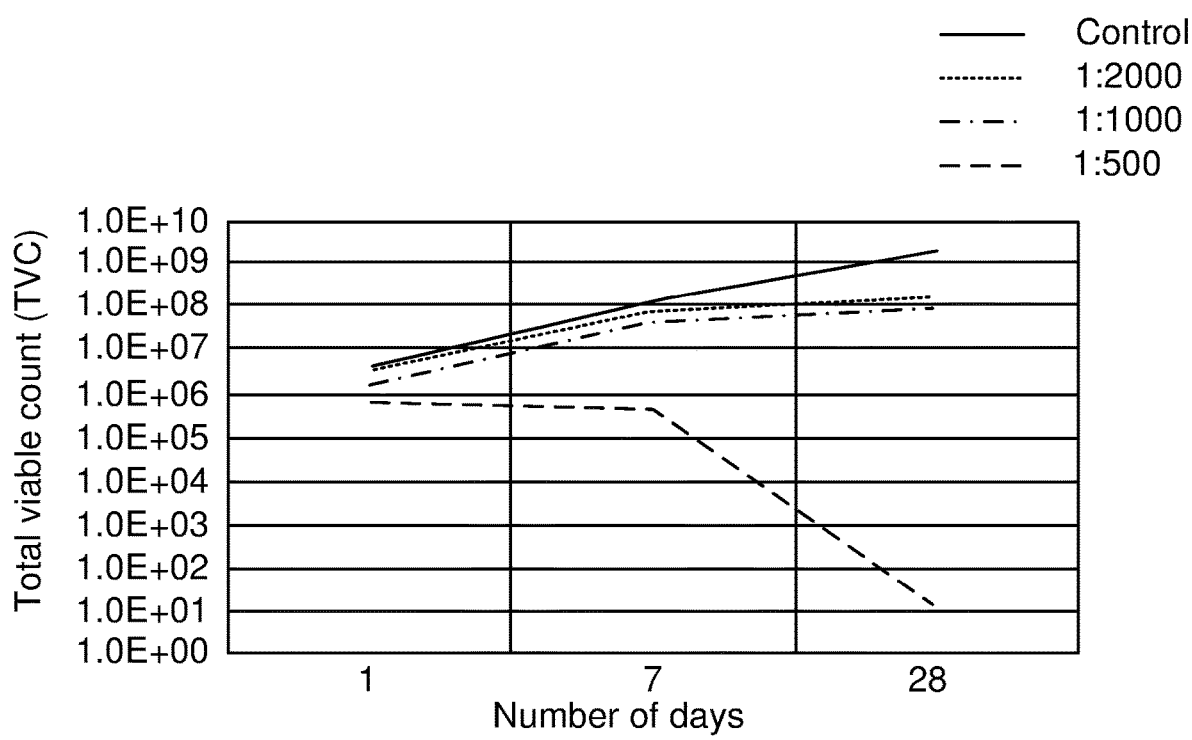
FIG. 1 shows the effect of different additions of the boron and/or boric acid containing additive on the growth of *Pseudomonas aeruginosa* in the water phase in a diesel water emulsion fuel sample, performed according to ASTM 1259-05. The results are shown as total viable count (TVC) at day 1, 7 and 28 plotted on a logarithmic scale. The results are based on a means value calculated from two samples.

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

The terms "biodegradable" and "biologically degradable" refers to the chemical degradation of a substance (lubricant) in the presence of micro-organisms/bacteria. There are two generally used measurements for biodegradability. The first is primary degradation, which is measured as the reduction of the carbon-hydrogen bond. This is determined with infrared spectroscopy (IR), which corresponds to the direct measure of the percentage of lubricant breakdown. The most widely used way to measure this degradation is by the Coordinating European Council (CEC) L-33-93 test method run for 21 days.

The other type of biodegradability measurement is secondary degradation, which is better known as ultimate biodegradability. This measures the evolution of carbon dioxide through the degradation process over a period of 28 days. The most common method used to determine ultimate biodegradability is by the Organization for Economic Cooperation and Development (OECD) 301B/ASTM D5864.

The benchmark for qualifying a lubricant as biodegradable is if its biodegradability is more than 80 percent by the CEC L-33-93 method or more than 60 percent by the OECD 301B method.

The term "boron" refers to the element boron, B, atomic mass 10.81 and "boric acid" refers to the compound $H_3BO_3$ with a molecular weight of 61.8 g/mol. The term "boron oxide" refers to the compound $B_2O_3$ with a molecular weight of 69.6 g/mol.

The abbreviation "ppm" refers to parts per million, and when referring to the concentration of boron, this is preferably calculated as weight per weight, based on the atomic mass of elemental boron. Without wishing to be bound by theory, the inventors speculate that the boron is present in the form of dissolved boric acid, nanoparticles of boric acid or a combination thereof.

Boron compounds and boron derivatives have a multitude of uses, ranging from being a component in heat-resistant glass (borosilicate) to use as a polishing agent (boron carbide). It is also well known that boric acid is mildly antiseptic, and boric acid solutions are widely used as an eye washer. Simultaneously, boron is known to be an essential micronutrient, vital to fertilization, fruit and seed production.

In the context of the present description, the expression "prevention of microbial growth" includes both a "killing off" and a "keeping clean" effect with regard to microbes.

It has now been surprisingly found that boron, when added in ppm concentrations in the form of a stable solution prevents microbial growth in biofuels, biodegradable hydraulic fluids and lubricants. In addition to preventing microbial growth, the addition of boron significantly reduces corrosion. This makes it possible to avoid the use of conventional biocides to alleviate the problem with microbial growth in biofuels, hydraulic fluids and lubricants. It also addresses the problem of corrosion associated with these fuels, hydraulic fluids and lubricants, allowing for a wider use of these renewable alternatives to products derived from fossil raw materials.

Again without wishing to be bound by any theory, the inventors contemplate that these effects are due to many factors, one important factor being an antimicrobial effect which surprisingly is present also at these extremely low concentrations of boron. It is however also contemplated that boron and/or boric acid when added in the form of a stable solution forms a tribolayer on metal surfaces, protecting the surface from corrosion and also preventing or at least reducing microbial adhesion.

This is an important finding, as microbiologically influenced corrosion (MIC)—a phenomenon also known as microbial corrosion or biological corrosion—is a significant problem in many areas. Several species of bacteria are known to cause MIC and materials susceptible to MIC include carbon steels, stainless steels, aluminum alloys and copper alloys. Some of these bacteria are frequently encountered in soil and water, and are difficult to avoid. For example anaerobic sulfate reducing bacteria are linked to many instances of accelerated corrosion to steel in shipping and offshore constructions. Aerobic iron and manganese oxidizing bacteria are linked to accelerated corrosion and pitting of stainless steels and welds.

MIC is a particular problem in the transport sector, where fuel storage tanks, distribution systems and fuel tanks in vehicles, including ships and airplanes, are prone to corrosion. Long storage times and variations in humidity frequently leads to condensation of moisture on the inside of tanks, and an accumulation of water ensues. The problem is now accentuated by the increasing use of renewable fuels and the current ongoing phase-out of toxic antimicrobial additives. The present disclosure therefore offers a surprising new approach to conserving biofuels.

In fact, MIC appears to be the main corrosion type observed for biodiesel systems, especially in the presence of moist air and the resulting accumulation of water. The biological origin of biodiesel is believed to be one of the primary reasons for the higher potential for supporting microbial activities, compared to fossil-based diesel.

The general understanding until now has been that an addition of a low concentration of boron is only effective to reduce friction and wear in combustion engines, but the antimicrobial and anti-corrosion effects in fuels and hydraulic fluids as seen by the present inventors have to the best knowledge of the inventors not previously been disclosed.

The present inventors have investigated how the addition of boron and/or boric acid prevents microbial growth, both in terms of the "killing off" and the "keeping clean" effects, and how it simultaneously reduces corrosion.

Different sources of boron can be used. It is for example possible to use a boron compound such as a crystalline boric acid, boron oxide, boron trioxide etc. It is however preferable to use an oxygen-bearing boron compound such as boric acid ($H_3BO_3$) of pharmaceutical quality, i.e. with a purity of preferably at least 99% and a molecular weight of 61.8 g/mol. An alternative is to use boron oxide ($B_2O_3$), with a molecular weight of 69.6 g/mol, also known as anhydrous boric acid, also of pharmaceutical quality, i.e. with a purity of preferably at least 99%. A stable boric solution where the boron and/or boric acid is completely dissolved or at least a stable solution without any particles larger than 100 nm is then prepared for example according to the methods set out in WO2010/134872, incorporated herein by reference.

This method involves vigorous mixing and a settling step. The boron is incorporated in an organic solvent or a fuel, preferably first incorporated in an alcohol and then diluted to the desired concentration using a hydrocarbon carrier and/or a fuel. Preferably said carrier is the same fuel as the fuel to which the additive is intended to be added, or a carrier compatible with this fuel, lubricant or hydraulic fluid to which the additive is to be added. Care needs to be taken that that the resulting solution in free from any particles larger than 100 nm.

Antimicrobial Effect

Without wishing to be bound by any theory, the inventors contemplate that the stable boron solution produced according to the methods disclosed in WO 2010/134872 is a key factor behind the surprising results. It is contemplated that complete dissolution of boron, the fact that the solution at least is free from any particles larger than 100 nm and/or the electrostatic charge of molecules and/or particles also contributes to the superior anti-microbial properties.

Thus, as a first aspect of this disclosure, the inventors disclose the use of an inorganic boron compound for conserving biofuel and biologically degradable hydraulic fluids and lubricants and/or preventing microbial growth in biofuel and biologically degradable hydraulic fluids and lubricants, wherein boron is added to said biofuel and/or hydraulic fluid and/or lubricant to give a final concentration of elemental boron in the interval of 1 to 100 ppm.

According to an embodiment of said first aspect, said biofuel is chosen from biogas, an ethanol/gasoline blend, ethanol, an methanol/gasoline blend, methanol, an ethanol/diesel blend, a biodiesel according to EN-590 or ASTM D 6751, a blend of biodiesel and petroleum-based diesel, or mixtures thereof.

According to a preferred embodiment, the boron is added in the form of a stable solution of boric acid and/or boron oxide in a solvent, free from any particles larger than 100 nm, and wherein said solution is added to give a final concentration of elemental boron in the interval of 1 to 100 ppm, preferably 1 to 75 ppm, more preferably 1 to 50 ppm, most preferably 1-10 ppm.

Most preferably, in particular where the biofuel is chosen from biogas, an ethanol/gasoline blend, ethanol, a methanol/gasoline blend, methanol, an ethanol/diesel blend, a biodiesel according to EN-590 or ASTM D 6751, a blend of biodiesel and petroleum-based diesel, or mixtures thereof, said boron is added to give a final concentration of elemental boron in the interval of 1-10 ppm.

According to a particular embodiment, wherein said biofuel is biogas, the boron is added in the form of a stable solution of boric acid or boron oxide in a solvent, free from any particles larger than 100 nm, and wherein said solution is applied on the surfaces of compressors, pumps, valves, pipes and storage tanks. It is contemplated that boron forms a tribolayer on the inner metal surfaces in contact with the biogas. This is believed to act against microbial growth in several ways, for example through the antimicrobial effect of boron and/or boric acid in a stable solution, and by preventing or reducing microbial adhesion to the surfaces.

According to another embodiment, wherein said biofuel is an ethanol/gasoline blend or ethanol, the boron is added to the biofuel in the form of a stable solution of boric acid or boron oxide in a solvent, free from any particles larger than 100 nm, and wherein said solution is added to give a final concentration of elemental boron in the interval of 1 to 10 ppm. It is contemplated that already a very low concentration of elemental boron in this form has advantageous effects in blended ethanol/gasoline fuels and ethanol fuels, for example a concentration of 1-8 ppm, or within an interval of 1-5 ppm, preferably 2-3 ppm.

According to a particular embodiment, wherein said biologically degradable hydraulic fluid is chosen from a hydraulic environmental triglyceride (HETG), a hydraulic environmental ester synthetic (HEES, a water insoluble synthetic ester), hydraulic environmental poly glycol (HEPG), and hydraulic environmental polyalphaolefins (HEPR).

Preferably said biologically degradable hydraulic fluid is a hydraulic fluid chosen from hydraulic fluids according to SS 155434 (National Swedish standard for hydraulic fluids).

In a variant of the use disclosed above and according to any one of the previous embodiments, the boron is added to the hydraulic fluid in the form of a stable solution of boric acid or boron oxide in a solvent free from any particles larger than 100 nm, and wherein said solution is added to give a final concentration of elemental boron in the interval of 1 to 100 ppm. It is contemplated that in particular this stable solution, and the absence of any particles larger than 100 nm, is advantageous for ensuring adhesion to surfaces, and an efficient antimicrobial effect both from the boron in solution possibly acting on the microbial metabolism and from the boron adhering to the surfaces of equipment in contact with the fluids, possibly preventing or reducing microbial adherence to the surfaces.

Preferably the stable boron solution is added to give a final concentration of elemental boron in the interval of 1-100 ppm. Preferably 1-50 ppm, and most preferably 1-10 ppm. It is however contemplated that already a very low concentration of boron has advantageous effects on biologically degradable hydraulic fluids, for example a concentration within an interval of 1-5 ppm, preferably 2-3 ppm.

According to another embodiment, said biologically degradable lubricant is chosen from a lubricant having a base oil chosen from a vegetable oil, a synthetic ester, and polyalkylene glycols.

Preferably the lubricant comprises a vegetable base oil chosen from rapeseed oil, soybean oil, sunflower oil, palm oil, and mixtures thereof.

Preferably said biologically degradable lubricant is a lubricant chosen from lubricants according to SS 155470 (National Swedish Standard for greases).

According to an embodiment, the boron is added to the lubricant in the form of a stable solution of boric acid or boron oxide in a solvent, free from any particles larger than 100 nm, and wherein said solution is added to give a final concentration of elemental boron in the interval of 1 to 100 ppm.

Prevention of Corrosion

A another aspect relates to the prevention and/or reduction of microbial growth and corrosion in engines, on surfaces and in equipment in contact with biofuels and/or biologically degradable hydraulic fluids and/or lubricants, such as equipment used to store, transport or dispense biofuels, biologically degradable hydraulic fluids and/or lubricants wherein a stable solution of boric acid is added to said biofuel and/or hydraulic fluid and/or lubricant to give a final concentration of elemental boron in the interval of 1 to 100 ppm.

According to an embodiment of said aspect, the biofuel is chosen from biogas, an ethanol/gasoline blend, ethanol, an methanol/gasoline blend, methanol, an ethanol/diesel blend, a biodiesel according to EN-590 or ASTM D 6751, a blend of biodiesel and petroleum-based diesel, or mixtures thereof.

Preferably the boron is added in the form of a stable solution of boric acid in a solvent, free from any particles larger than 100 nm, and wherein said boron is added to give a final concentration of elemental boron in the interval of 0.1 to 50 ppm.

More preferably the boron is added to give a final concentration of elemental boron in the interval of 1-10 ppm. It is however contemplated that already a very low concentration of boron has advantageous effects biologically degradable hydraulic fluids, for example a concentration within an interval of 1-5 ppm, preferably 2-3 ppm.

According to another embodiment, the biofuel is biogas, the boron is added in the form of a stable solution of boric acid or boron oxide in a solvent, free from any particles larger than 100 nm, and wherein said solution is applied on the surfaces of compressors, pumps, valves, pipes and storage tanks where corrosion prevention is needed. It is suggested by the inventors that boron is either added intermittently, in higher concentrations or continuously, in lower concentrations. In this context, a "higher" concentration is in the order of magnitude of 100 or 1000 ppm, for example about 100, 200, 300, 400, 500 ppm, or about 1000, 2000, 3000, 4000 and 5000 ppm, whereas a "lower" concentration is in the order of magnitude of 1 or 10 ppm, for example about 1, 2, 3, 4, or 5 ppm or about 10, 20, 30, 40 or 50 ppm.

According to another embodiment, where the biofuel is an ethanol/gasoline blend or ethanol, the inorganic boron compound is added to the biofuel in the form of a stable solution of boric acid or boron oxide in a solvent, free from any particles larger than 100 nm, and wherein said solution is added to give a final concentration of elemental boron in the interval of 0.1-10 ppm In another embodiment, said biologically degradable hydraulic fluid is chosen from a hydraulic environmental triglyceride (HETG), a hydraulic environmental ester synthetic (HEES, a water insoluble synthetic ester), hydraulic environmental poly glycol (HEPG), and hydraulic environmental polyalphaolefins (HEPR).

In one embodiment, said biologically degradable hydraulic fluid is a hydraulic fluid chosen from hydraulic fluids according to SS 155434 (National Swedish standard for hydraulic fluids).

Preferably the boron is added to the hydraulic fluid in the form of a stable solution of boric acid or boron oxide in a solvent, free from any particles larger than 100 nm, and wherein said solution is added to give a final concentration of elemental boron in the interval of 1-100 ppm. It is contemplated that in particular this stable solution, and the absence of any particles larger than 100 nm, is advantageous for ensuring adhesion to surfaces, and an efficient antimicrobial effect both from the boron compounds in solution and from the boron adhering to the surfaces of equipment in contact with the hydraulic fluids.

Most preferably the boron is added to give a final concentration of elemental boron in the interval of 1-10 ppm.

According to another embodiment, said biologically degradable lubricant is chosen from a lubricant having a base oil chosen from a vegetable oil, a synthetic ester, and polyalkylene glycols.

Preferably the lubricant comprises vegetable base oil chosen from rapeseed oil, soybean oil, sunflower oil, palm oil, and mixtures thereof.

According to an embodiment, said biologically degradable lubricant is a lubricant chosen from lubricants according to SS 155470 (National Swedish Standard for greases).

In the above embodiments, the boron is added to the lubricant in the form of a stable solution of boric acid or boron oxide in a solvent, free from any particles larger than 100 nm, and said solution is added to give a final concentration of elemental boron in the interval of 1 to 100 ppm.

New Fuel Blends

The current findings of the inventors make it possible to develop new fuel blends, where the problems of microbial growth and corrosion can be addressed, minimized or even prevented without resorting to toxic chemical additives. This is particularly advantageous for biodegradable or environmentally friendly fuels.

A fifth aspect relates to a gasoline-based fuel blend comprising at least 5% ethanol and 1-10 ppm elemental boron, preferably in the form of an inorganic boron compound.

A sixth aspect relates to a gasoline-based fuel blend comprising at least 5% methanol and 1-10 ppm elemental boron, preferably in the form of an inorganic boron compound.

A seventh aspect relates to a biodiesel fuel blend comprising 1-10 ppm elemental boron, preferably in the form of an inorganic boron compound.

Killing Off v. Keeping Clean

In addition to new fuel blends, the present inventors also disclose two alternative or complementary uses of boron and/or boric acid: According to one aspect, an addition of boron is made to kill microbes and disperse sludge and deposits in tanks and pipes in contact with a fuel prone to microbial contamination and growth. According to this aspect, a higher dose is used at regular intervals, for example before, during or after maintenance. It should be kept in mind that this treatment of the fuel system can lead to the clogging of filters and fuel pumps and injectors, as microbial deposits are removed from the tanks and pipes.

According to another aspect, boron is incorporated in the fuel in order to keep tanks and pipes clean. In this aspect, a lower dose is preferably incorporated in the fuel from the start and throughout the distribution chain, during storage and use. This has the added advantage of prevention microbial growth and reducing corrosion during the entire chain of transport and handling, storage, distribution, and dispensing the fuel from production to end-user. This function of "keeping clean" can be seen as a subset of "conserving" the fuel, an important factor in the long-time storage of fuels.

In the context of the above two aspects, a "higher" concentration is a concentration in the order of magnitude of a multiple of 100 or 1000 ppm, for example about 100, 200, 300, 400, 500 ppm, or about 1000, 2000, 3000, 4000 and 5000 ppm, whereas a "lower" concentration is in the order of magnitude of 1 or 10 ppm, for example about 1, 2, 3, 4, or 5 ppm or about 10, 20, 30, 40 or 50 ppm.

Biologically Degradable Hydraulic Fluids and Lubricants

An eight aspect relates to biologically degradable hydraulic fluids comprising 1-100 ppm boron, preferably 1 to 75 ppm, more preferably 1 to 50 ppm, most preferably 1-10 ppm. It is however contemplated that already a very low concentration of boron has advantageous effects on biologically degradable hydraulic fluids, for example already at a concentration within an interval of 1-5 ppm, preferably 2-3 ppm. The boron is preferably added in the form of a stable solution of an inorganic boron compound.

A ninth aspect relates to a biodegradable lubricant comprising a vegetable base oil and 1-100 ppm boron, preferably 1 to 75 ppm, more preferably 1 to 50 ppm, most preferably 1-10 ppm. It is however contemplated that already a very low concentration of boron has advantageous effects on biologically degradable hydraulic fluids, for example a concentration within an interval of 1-5 ppm, preferably 2-3 ppm. The boron is preferably added in the form of a stable solution of an inorganic boron compound.

One significant advantage is that microbial growth can now be prevented using a non-toxic additive, and additionally an additive which has other advantageous properties. It is clear that a combination of reduced or prevented microbial growth and reduced corrosion is a significant advantage. The friction reducing properties of boron have been known for a long time, but not in this context. The combined effects are also very surprising. In particular the long term effect is likely to be attributable to the controlled particle size and/or the electrostatic charge of the particles.

An additional advantage is that boron, unlike many other compounds that have been used or are suggested for use as anti-microbial additives, is non-toxic and has no known impact on the environment.

Boron compounds are generally considered as non-toxic at levels normally encountered, and boron compounds are widely used in cosmetics, products for oral hygiene, bath products and products for waving hair. In these applications, the allowed concentration (expressed as boric acid) ranges from 0.1 to 18%, which is significantly higher than the ppm concentrations disclosed herein.

According to the "Opinion on Boron Compounds issued in 2010 by the Scientific Committee on Consumer Safety (SCCS/1249/09), boric acid is considered non-mutagenic based on the available in vitro data. No data regarding a possible association between cancer and boron exposure in humans has been found. In fact, different boron compounds and in particular boric acid is already widely used in cosmetics and healthcare products. Thus, replacing toxic organic biocides with a boron and/or boric acid based compound offers a surprising and significant advantage. Unlike organic biocides which are prone to accumulating in the food chain, boron and/or boric acid has no known environmental impact and is thus well suited also for sensitive environments, marine use, as well as use in forestry and agriculture.

Interestingly, a boron and/or boric acid based product produced according to WO 2010/134872 has been certified under the ISO 21469 standard for lubricants for use in specialized industries such as food, pharmaceuticals, cosmetics and animal feed manufacturing.

Notably, without this inventive use of inorganic boron compounds, disclosed herein, the environmental benefits of using a biodegradable lubricant or hydraulic fluid would easily be off-set by the potential hazards associated with the organic biocides normally used to prevent microbial growth in such products.

Further, the conserving, long-term effect of boron and/or boric acid on fuels, hydraulic fluids and lubricants, when added in the form of a stable solution, is a surprising advantage. In addition to the environmental friendliness of boron and/or boric acid, the low cost and easy availability of these substances make this an excellent anti-microbial, conserving and/or preserving additive for biofuels, hydraulic fuels and lubricants containing renewable components.

Other advantages of boron in the context of its surprising antimicrobial and corrosion reducing or corrosion preventing effects in more environmentally friendly fuels, and biologically degradable and more environmentally friendly hydraulic fluids and lubricants will be evident from a closer study of the description, examples and claims.

EXAMPLES

Example 1

A Comparative Example

The inventors have tested whether an addition of boron at levels described in the embodiments would be effective to prevent microbial growth in a biodiesel sample containing water. 10 liters of Shell City Diesel F Environment 0.001 S (CAS No: 64742-47-8) was purchased. According to the manufacturer's Material Safety Data Sheet, the water content of this product is below a maximum of 60 mg/kg. Two samples of 100 ml were placed in separate open glass jars and 10 ml tap water was added to both samples. A stable boron solution was added to one sample to give a final boron concentration of about 7 ppm.

Both samples were stored at room temperature for 25 days while the microbial growth was observed. In the untreated sample, microbial growth soon became visible as a clouding or turbidity in the untreated sample. At the end of the test period, the untreated sample was turbid and practically opaque, while the boron-containing sample remained clear and unchanged.

Example 2

Evaluation of Antimicrobials in Liquid Fuels Boiling Below 390° C. According to ASTM E 1259-05

The inventors commissioned a series of tests according to ASTM 1259-05 where diesel fuel samples were inoculated with test organisms known to cause problems in diesel fuel. For the test, a sample of commercial diesel fuel was first mixed with a small quantity of water and then infected with a certain quantity of microorganisms. The test organisms and the amounts added are presented in Table 1.

TABLE 1

Test organisms and initial inoculum

| Organism | Culture | Type | Initial inoculum (cfu/ml) |
|---|---|---|---|
| Pseudomonas aeruginosa | DSM 15980 | Bacteria | $5.0 \times 10^6$ |
| Hormoconis resinae | DSM 1203 | Fungus | $3.0 \times 10^5$ |
| Yarrowia tropicalis | DSM 11953 | Yeast | $1.2 \times 10^6$ |

The inventive additive was added to the fuel samples in the mixing ratios presented in Table 2, corresponding to the boric acid and boron concentrations as disclosed below.

TABLE 2

Mixing ratios and corresponding concentration of boron and boric acid

| Mixing ratio | 1:500 | 1:1000 | 1:2000 |
|---|---|---|---|
| Boric acid concentration (ppm) | 174 | 88 | 44 |
| Boron concentration (ppm) | 30 | 15 | 7.5 |

Figure 2:
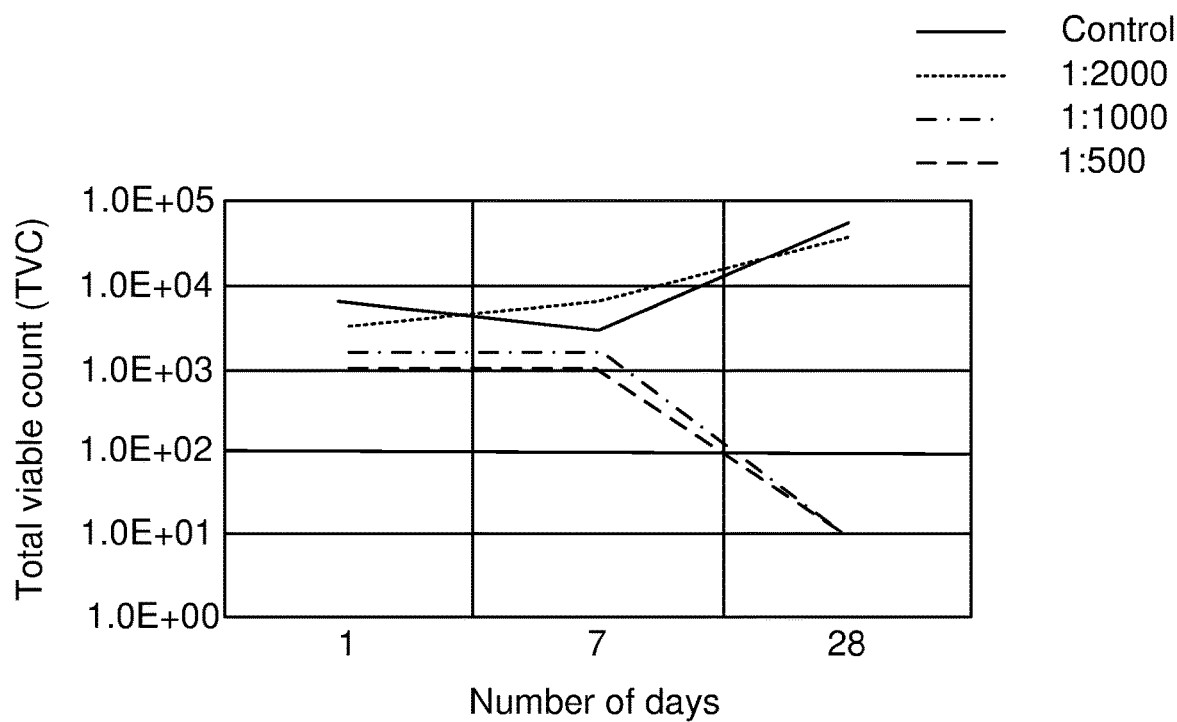
FIG. 2 shows the effect of different additions of the boron and/or boric acid containing additive on the growth of *Hormocoris resinae* in the water phase in a diesel water emulsion fuel sample, performed according to ASTM 1259-05. The results are shown as total viable count (TVC) at day 1, 7 and 28 plotted on a logarithmic scale. The results are based on a means value calculated from two samples.
Figure 3:
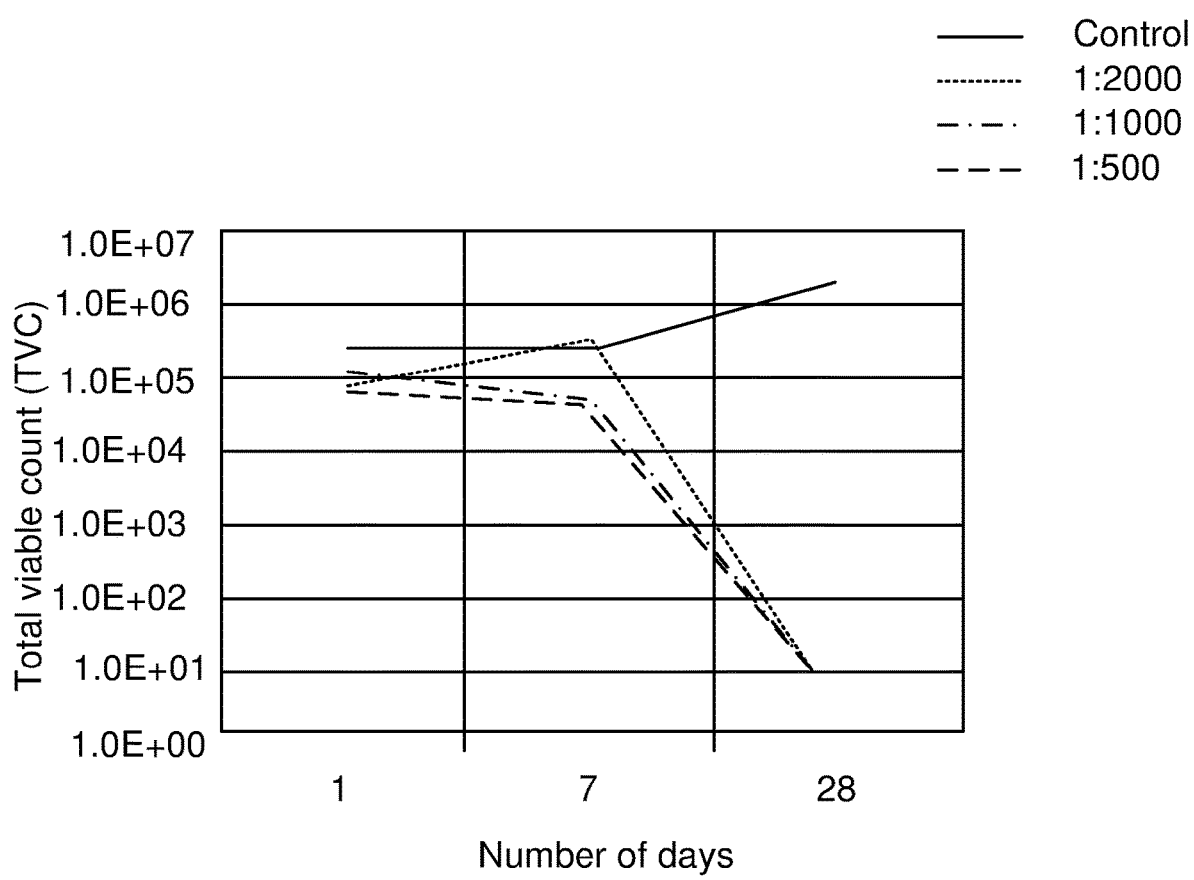
FIG. 3 shows the effect of different additions of the boron and/or boric acid containing additive on the growth of *Yarrowia tropicalis* in the water phase in a diesel water emulsion fuel sample, performed according to ASTM 1259-05. The results are shown as total viable count (TVC) at day 1, 7 and 28 plotted on a logarithmic scale. The results are based on a means value calculated from two samples.

The results are shown in FIGS. 1, 2 and 3. The largest reduction in growth for all three types of microorganisms was seen when the inventive additive was used in a mixing ratio of 1:500, corresponding to 30 ppm boron, or 174 ppm boric acid. By comparison, the recommended booster dose when using the commercial marine diesel protection additive was 1:200.

At a mixing ratio of 1:1000, the inventive additive was still highly effective against both *Hormoconis resinae* and *Yarrowia tropicalis*. This mixing ratio corresponds to 15 ppm boron or 88 ppm boric acid. At a mixing ratio of 1:2000, corresponding to 7.5 ppm boron or 44 ppm boric acid, the inventive additive was still effective against *Yarrowia tropicalis*.

Notably, the growth of microorganisms is reduced for all the tested mixing ratios, compared to control. The test confirms that the inventive additive works well also under standardized testing conditions (ASTM 1259-05) and importantly, that an effect is achieved entirely without using organic biocides. In marine applications, the avoidance of organic biocides is particularly important, as these may accumulate in marine organisms and accumulate in the food chain.

The inventive additive was compared to a commercial marine diesel protection additive containing organic biocidic ingredients. The commercial product was added in a mixing ratio of 1:200 and 1:1000 according to the manufacturer's recommendations. The mixing ratios correspond to a booster dose for systems which are already contaminated, and a preventive dose for the maintenance of clean or already treated systems.

The tests showed as expected that the commercial biocide was effective against all three test organisms, and reduced them to below detection levels. After a contact time of 21 days, no microbial growth could be detected in the fuel phases of the samples. In the water phases, the amounts of test organisms were reduced to below the detection limits.

In summary, the comparative tests show that the non-toxic inventive additive has an effect against typical sludge causing microorganism in a similar time frame as the tested commercial biocidic products, but without posing any risk to the users. Further, in the case of a spill, the inventive additive does not have any negative consequences on the environment.

Example 3

Corrosion Reducing Effects of the Boron Additive

The above results indicate that already a very low boron concentration has a significant antimicrobial effect, and in addition ongoing laboratory experiments show a corrosion reducing effect.

Without wishing to be bound by theory, the inventors contemplate that this is due to a surprising synergistic effect. The boron and/or boric acid not only has an antimicrobial effect in solution, it also reduces or prevents microbes from adhering to surfaces, where the microbes could create an oxidative environment. Further, it is contemplated that the boron and/or boric acid forms a tribolayer on the inner metal surfaces in contact with the biogas. This is believed to act against microbial growth in several ways, for example through the antimicrobial effect of boron and/or boric acid in a stable solution, and by preventing or reducing microbial adhesion to the surfaces.

Example 4

Real-Life Long Term Tests

The effect of the addition of a stable boron solution to the fuel tank of a ship has been investigated under real-life conditions. Onboard a ship, the humid sea air and the changing temperatures tend to result in the condensation of water in the fuel tank, and microbial growth is frequently a problem. When the microbial growth is uncontrolled, it can result in large amounts of slime in the fuel-water interface, deposits on tank walls and in pipes. These can travel in the fuel system and clog filters and valves, causing engine malfunction and necessitating time-consuming overhaul. Microbial growth can also lead to reduced fuel stability and corrosion.

In one experiment, a stable boron solution was added to the marine diesel fuel to give a final concentration of approximately 15 ppm boron in the fuel. After a test period of 2.5 months, the fuel tank and fuel filters were inspected, and a marked improvement was noted. The test user reported that after the test, they had fewer problems with clogged filters. This is most likely due to the tanks being much cleaner than before the test started. The test user reported that apart from clogged filters, the engines were running flawlessly through out the test.

A noticeable difference in smoke level and soot was also reported. Both increased significantly when not using the additive, indicating that the additive also improved combustion. In this test, the ability to measure fuel consumption was very limited, so no change in consumption could be registered. The experiment however showed the long term positive effects of the boron additive also under difficult, real life conditions.

In another long term test, where a stable boric acid solution was mixed into the diesel fuel during approximately 1500 engine hours on both the main engine (Volvo Penta) and the diesel generator. At the end of the test period, the user reported that the diesel tank had remained very clean. Additionally the user recorded a significant decrease in diesel consumption, and also a reduction of soot and smoke.

Example 5

Preventing Microbial Growth in HVO and RME

The inventors have initiated a test using commercial biofuels, rapeseed methyl ester (RME) and hydrotreated vegetable oil (HVO). 20 samples were prepared, 10×50 g of each fuel type, HVO and RME respectively. For each fuel type, there were four boron concentrations and a reference. One of each concentration and fuel was placed in a heating chamber at 45° C. and in front of a window subjected to sunlight.

Water was taken from a lake nearby and stored in the heat chamber for an amount of time to enhance microorganism content and activity. 15 g of lake water was added to each sample, and the contaminated samples stored one week in 45° C. and exposed to sunlight.

A stable solution of inorganic boron in ethanol was added to each sample in different dilutions, corresponding to the theoretical concentrations in the samples shown in table 3:

TABLE 3

Mixing ratios and corresponding approximate concentrations of boric acid and EtOH

| Mixing ratio | Boric acid concentration (ppm) | Boron concentration (ppm) | EtOH concentration (ppm) |
| --- | --- | --- | --- |
| 1:500 | 176 | 30 | 1824 |
| 1:1000 (different batch) | 105 | 18 | 894 |
| 1:1000 | 88 | 15 | 912 |
| 1:2000 | 44 | 7.5 | 456 |

The initial results indicate that also the lowest tested concentration of boric acid has a marked effect on microbial growth in the contaminated samples.

Without further elaboration, it is believed that a person skilled in the art can, using the present description, including the examples, utilize the present invention to its fullest extent. Also, although the invention has been described herein with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for prevention of microbial growth and microbiologically influenced corrosion (MIC) in equipment used for storage and/or transportation of a biofuel, the method comprising applying boron to inner surfaces of compressors, pumps, valves, pipes and storage tanks used in distributing and storing the biofuel by adding boron to said biofuel in the form of a stable solution of boric acid in a solvent, free from any particles larger than 100 nm, wherein said boron is added to give a final concentration of elemental boron in said biofuel in an interval of 1 to 50 ppm, and wherein said biofuel is chosen from biogas, an ethanol/gasoline blend, ethanol, a methanol/gasoline blend, methanol, an ethanol/diesel blend, a biodiesel according to EN-590 or ASTM D 6751, a blend of biodiesel and petroleum-based diesel, or mixtures thereof.

2. The method according to claim 1, wherein said biofuel is biogas.

* * * * *